United States Patent [19]

Burn et al.

[11] 4,062,955
[45] Dec. 13, 1977

[54] ANALGESIC BASIC NAPHTHALENE DERIVATIVES

[75] Inventors: Derek Burn, Stoke Poges; Richard J. Coles, Uxbridge, both of England

[73] Assignee: Glaxo Laboratories Limited, Greenford, England

[21] Appl. No.: 625,863

[22] Filed: Oct. 28, 1975

[30] Foreign Application Priority Data

Nov. 4, 1974 United Kingdom ............... 47589/74

[51] Int. Cl.$^2$ .................. A61K 51/535; C07D 295/12
[52] U.S. Cl. .................. 424/248.56; 544/79; 544/107; 544/108; 544/111; 544/124; 544/129; 544/162; 260/239 B; 260/268 B; 260/293.64; 260/570.8 R; 260/570.5 P; 260/570.9
[58] Field of Search .................. 260/246 B, 247.5 R, 260/247.5 G, 247.5 D, 247.5 FP; 424/248, 248.56

[56] References Cited

U.S. PATENT DOCUMENTS 2,040,040 5/1960 Bruson .......................... 260/246 B

FOREIGN PATENT DOCUMENTS 1,003,219 4/1955 Germany.

OTHER PUBLICATIONS

Dean et al., J. Chem. Soc. pp. 2065–2069, (1968).
G. Wittig et al., Annalen, pp. 55–76, 589, (1954).
Badger et al., Nature p. 21, 162 (1948).
Gornostaeva et al., Chemical Abstracts, vol. 54, 24473h, (1960).
Reid et al., Chemical Abstracts, vol. 53, 6241f, (1959).

*Primary Examiner*—Donald G. Daus
*Assistant Examiner*—Jose Tovar
*Attorney, Agent, or Firm*—Bacon & Thomas

[57] ABSTRACT

Compounds of the general formula:

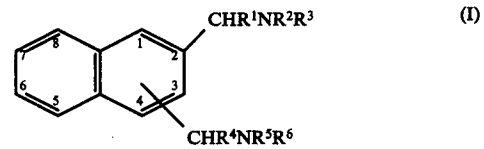

wherein the groups $CHR^1NR^2R^3$ and $CHR^4NR^5R^6$ may be the same or different and where the group $CHR^4NR^5R^6$ is in either the 1 or the 3 position and $R^1$ and $R^4$ independently represent a hydrogen atom or an aryl group;

$R^2$, $R^3$, $R^5$ and $R^6$ which may be the same or different are each a hydrogen atom or an alkyl group or an aryl group both of which may in turn be substituted by one or more hydroxy, alkoxy, acyloxy, dialkylamino or aryl groups or the groups —$NR^2R^3$ and/or $NR^5R^6$ represent a heterocyclic ring containing one or more hetero atoms and which ring may optionally be substituted by an alkyl, aryl or aralkyl group and in which either aromatic ring of the naphthalene nucleus may be further substituted; with the proviso that when $R^1$, $R^4$, $R^2$ and $R^5$ are hydrogen, then $R^3$ and $R^6$ cannot both be benzyl, when the second substituent is in the 1 position; and when $R^1$ and $R^4$ are hydrogen, then $R^2$, $R^3$, $R^5$ and $R^6$ cannot all be methyl when the second substituent is in the 1 position; and when $R^1$ and $R^4$ are hydrogen, then $R^2$ and $R^3$ and $R^5$ and $R^6$ together with the nitrogen atom cannot both be piperidino when the second substituent is in the 3 position and the naphthalene nucleus is further substituted by hydroxy in the 1 and 4 positions; and pharmaceutically acceptable salts of such compounds; and hydrates of such compounds and such salts. The compounds have activity on the central nervous system in particular as analgesics.

29 Claims, No Drawings

ANALGESIC BASIC NAPHTHALENE DERIVATIVES

This invention relates to novel naphthalene derivatives having pharmacological activity and to the production thereof and to pharmaceutical compositions containing such compounds.

It has been found that certain naphthalene derivatives of formula I below have interesting pharmacological activity. Thus, the compounds have activity on the central nervous system in particular as analgesics.

Accordingly, the invention provides compounds of the following general formula (I):

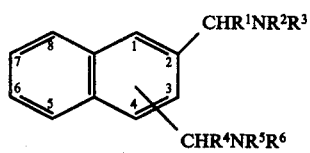

wherein the groups $CHR^1NR^2R^3$ and $CHR^4NR^5R^6$ may be the same or different and where the group $CHR^4NR^5R^6$ is in either the 1 or the 3 position and $R^1$ and $R^4$ independently represent a hydrogen atom or an aryl group.

$R^2$, $R^3$, $R^5$ and $R^6$ which may be the same or different are each a hydrogen atom or an alkyl group or an aryl group both of which may in turn be substituted by one or more hydroxy, alkoxy, acyloxy, dialkylamino or aryl groups or the groups $-NR^2R^3$ and/or $NR^5R^6$ represent a heterocyclic ring containing one or more hetero atoms and which ring may optionally be substituted by an alkyl, aryl or aralkyl group.

Preferred meanings for the groups $R^2$, $R^3$, $R^5$ and $R^6$ of those meanings specified above are hydrogen, alkyl or hydroxyalkyl and for $NR^2R^3$ and $NR^5R^6$ the specified heterocyclic rings, in particular a 5, 6 or 7 membered heterocyclic ring which may contain additional nitrogen or oxygen atoms, and which may optionally be substituted by alkyl, aryl or aralkyl groups.

In the above general formula either aromatic ring of the naphthalene nucleus may be further substituted by one or more additional groups, in particular by alkyl, trifluoromethyl, alkoxy, halogen, hydroxy, acyloxy and aryl groups. Preferably the substituents are alkyl, alkoxy, halogen or aryl.

The terms alkyl and alkoxy as applied to substituent groups and parts of substituent groups as used herein means lower alkyl and lower alkoxy containing 1 to 6 carbon atoms, preferably 1 to 4 carbon atoms. Acyloxy means lower alkanoyloxy, including formyloxy. Aryl preferably indicates phenyl.

The invention also provides pharmaceutically acceptable salts of these compounds such as salts with pharmaceutically acceptable organic and inorganic acids e.g. hydrochloric, salicylic etc. and quaternary salts e.g. methiodide. It is to be understood that the compounds may exist as hydrates and the invention therefore extends to such hydrates.

Preferred compounds according to the invention are those in which $R^1$ is hydrogen or phenyl, ane one of the groups $R^2$ and $R^3$ is alkyl, in particular methyl, ethyl, propyl, n-butyl, which may be optionally substituted by hydroxy, the other group $R^2$ or $R^3$ being hydrogen or alkyl or $R^2$ and $R^3$ together with the adjacent nitrogen atom represent piperidino, morpholino, pyrrolidinyl, piperazinyl, tetrahydropyridino or hexamethyleneimino which groups may be substituted with one or more methyl or phenyl groups. Representative substituted heterocyclic rings are:

2,6-dimethylmorpholino;
2-, 3- and 4-methylpiperidino;
N'-methyl and N'-phenylpiperazinyl.

The meanings for $R^4$, $R^5$ and $R^6$ may be the same as for $R^1$, $R^2$ and $R^3$ respectively or they may be different.

The other substituents on the aromatic rings of the naphthalene nucleus are preferably alkoxy containing one to six carbon atoms e.g. methoxy, ethoxy and butoxy, and preferably one or two such groups are present. Other preferred substituents include aryl groups, e.g. phenyl, or alkyl groups, in particular lower alkyl groups, containing 1 to 6 carbon atoms e.g. methyl and halogen atoms e.g. fluorine, bromine or chlorine. Preferably such additional substituents are present in the 1-position, 4-position, 5-position and/or 6-position. Two or more such substituents may be present.

Some of the compounds falling within the above formula are known. These are set out in the table below.

| X | Y | Substituents in aromatic ring | |
|---|---|---|---|
| 2-CH$_2$NMe$_2$ | 1-CH$_2$NMe$_2$ | — | — |
| 2-CH$_2$NHCH$_2$Ph | 1-CH$_2$NHCH$_2$Ph | — | — |
| | | 1-OH | 4-OH |
| 2-CH$_2$N⟩ | 3-CH$_2$N⟩ | | |

It has not been suggested in the literature that these have the pharmacological properties which we have found them to have. The general formula above insofar as they cover these known compounds is not to be construed as covering them per se but only covering them when in the form of a pharmaceutical composition that is in association with a pharmaceutically acceptable carrier, and to methods of treatment of conditions susceptible to treatment by the use of such compounds.

The definition of the compounds in formula (I) insofar as it covers new compounds is therefore subject to the proviso that when $R^1$, $R^4$, $R^2$ and $R^5$ are hydrogen, then $R^3$ and $R^6$ cannot both be benzyl, when the second substituent is in the 1 position; and when $R^1$ and $R^4$ are hydrogen, then $R^2$, $R^3$, $R^5$ and $R^6$ cannot all be methyl when the second substituent is in the 1 position; and when $R^1$ and $R^4$ are hydrogen, then $R^2$ and $R^3$ and $R^5$ and $R^6$ together with the nitrogen atoms cannot both be piperidino when the second substituent is in the 3 position and the naphthalene nucleus is further substituted by hydroxy in the 1 and 4 positions.

The compounds according to the invention may be made by a number of processes.

One process which is particularly useful for the preparation of compounds of formula (I) involves the reaction of compounds of formula (II):

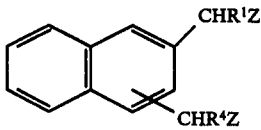

(II)

where Z represents a leaving group. Suitable leaving groups are halogen e.g. chlorine, bromine or iodine, acyloxy, e.g. acetoxy and sulphonyloxy, e.g. tosyloxy and the group $CHR^4Z$ is in the 1 or 3 position, with an excess of an amine of formula $HNR^2R^3$ where $R^2$ and $R^3$ have the meanings given above optionally in the presence of a solvent, and if desired, with heating. This reaction produces compounds in which $R^5$ is the same as $R^2$ and $R^6$ is the same as $R^3$ and where $R^2$ and $R^3$ and hence $R^5$ and $R^6$ may be the same or different.

The compounds of formula (II) may be prepared by standard means. For example where Z is halogen this standard method may consist in halogenation of a dialkyl derivative of naphthalene. Where Z is halogen compounds of formula (II) may also be prepared from a bis (hydroxyalkyl) derivative of formula (III):

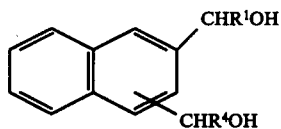

(III)

where $R^1$ and $R^4$ have the meanings specified above, by treatment with a halogenating agent. Compounds of formula (II) where Z represents an acyloxy or sulphonyloxy group may be prepared by treatment of the compound of formula (III) with a suitable acylating or sulphonylating agent. Suitable bis(hydroxyalkyl) derivatives where $R^1$ and $R^4$ are hydrogen may conveniently be prepared for example by reduction of a dicarboxylic acid of formula (IV) or a corresponding ester or anhydride thereof:

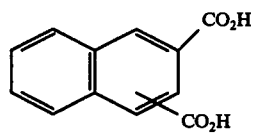

(IV)

A method for the production of hydroxyalkyl derivatives of formula (III) in which $R^1$ and $R^4$ are phenyl is described in connection with Examples 24 and 25 herein.

In another process for the preparation of compounds of formula (I) in which $R^1$ and $R^4$ are hydrogen a diamide of formula (V):

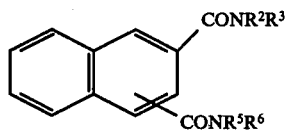

(V)

where $R^2$, $R^3$, $R^5$ and $R^6$ have the meanings given above, is reduced in the presence of a suitable reducing agent for example diborane or a complex metal hydride, such as lithium aluminum hydride or sodium dihydro bis-(2-methoxyethoxy) aluminate in an inert solvent. Inert solvents include ethers e.g. tetrahydrofuran and aromatic hydrocarbons. This process is particularly applicable to those compounds in which the group $-NR^2R^3$ is the same as the group $NR^5R^6$. The diamide (V) may be conveniently prepared either directly from the diacid of formula (IV) or indirectly via the diester or the diacid chloride thereof, by reaction with an amine of formula $HNR^2R^3$, where $R^2$ and $R^3$ have the meanings given above. It is possible to prepare a diamide of formula (V) in which $-NR^2R^3$ is different from $-NR^5R^6$ by treating the anhydride of the acid (IV) successively with different amines $HNR^2R^3$ and $HNR^5R^6$.

In a further process for the preparation of compounds of formula (I), particularly where $R^1=R^4=$hydrogen and where the groups $R^2$, $R^3$, $R^5$ and $R^6$ may be the same or different, a compound of formula (VI):

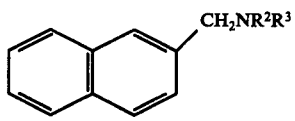

(VI)

where $R^2$ and $R^3$ have the meanings given above or represents groups convertible thereto, is reacted with an organometallic reagent, for example an organolithium, particularly butyl lithium, to form a metallic derivative e.g. the lithio derivative which is then reacted with an alkyl halide of formula $ZCH_2NR^5R^6$ where Z, $R^5$ and $R^6$ have the meanings given above or are groups convertible thereto, to give the diamine of formula (I).

In a further process for the preparation of compounds of formula (I) applicable preferably to the case where $R^1=R^4=$hydrogen and wherein the groups $R^2$, $R^3$, $R^5$ and $R^6$ may be the same or different, and have the meanings defined, except that $R^2$ and $R^3$ cannot be hydrogen, a dihalide of formula (II) wherein $R^1=R^4=$hydrogen is reacted with an amine of formula $HNR^2R^3$ wherein the two groups $R^2$ and $R^3$ are defined as above but cannot be hydrogen, in a solvent, such as an alkanol e.g. ethanol under controlled conditions to obtain a quaternary salt of formula (VII):

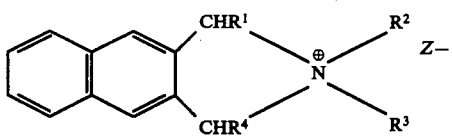

(VII)

where Z have the meaning given and $R^1$, $R^4$, $R^2$ and $R^3$ have the meanings defined above except that $R^2$ and $R^3$ cannot be hydrogen. This salt is subsequently reacted with another amine of formula $HNR^5R^6$, where $R^5$ and $R^6$ are defined as above, optionally in the presence of an inert solvent to give the compounds of formula (I).

The compounds of formula (I) may be formulated in association with pharmaceutical non-toxic carriers or diluents and may be presented in liquid, solid or semiliquid form, for administration, and the invention extends to such pharmaceutical compositions.

Preferably the compositions are presented in a form suitable for oral administration, i.e. in the form of tablets, capsules or the like or as granules formulated with a sweetening agent such as sucrose and a flavouring agent, said granules being reconstitutable with water if desired, or as a syrup. In particular they are preferably presented in a form of a dosage unit, advantageously in the form of a tablet or capsule, containing an amount of the active ingredient within the range of 5-100 mg per dosage unit when used for their effect on the central nervous system. The pharmaceutical compositions may contain other active ingredients.

The compounds given in Table 1 below were prepared similarly, from the indicated starting materials.

Table 1

| Example | Starting Material/Base | Product |
|---|---|---|
| 2 | 1,2-Bis(bromomethyl)naphthalene/morpholine | 1,2-Bis(morpholinomethyl)naphthalene dihydrochloride, m.p. 248° |
| 3 | 1,2-Bis(bromomethyl)naphthalene/piperidine | 1,2-Bis(piperidinomethyl)naphthalene dihydrochloride, m.p. 240° |
| 4 | 1,2-Bis(bromomethyl)naphthalene/ethylamine | 1,2-Bis(ethylaminomethyl)naphthalene dihydrochloride, m.p. 286° |
| 5 | 1,2-Bis(bromomethyl)naphthalene/3-aminopropanol | 1,2-Bis(3'-hydroxypropylaminomethyl)naphthalene dihydrochloride m.p. 240° |
| 6 | 2,3-Bis(bromomethyl)naphthalene/N-Ethyl-N-methylamine | 2,3-Bis(N-ethyl-N-methylaminomethyl)naphthalene dihydrochloride, m.p. 176° |
| 7 | 2,3-Bis(bromomethyl)naphthalene/methylamine | 2,3-Bis(methylaminomethyl)naphthalene dihydrochloride, m.p. 288° |
| 8 | 2,3-Bis(bromomethyl)naphthalene/dimethylamine | 2,3-Bis(dimethylaminomethyl)naphthalene dihydrochloride, m.p. 244° |
| 9 | 2,3-Bis(bromomethyl)naphthalene/diethylamine | 2,3-Bis(diethylaminomethyl)naphthalene dihydrochloride, m.p. 218° |
| 10 | 2,3-Bis(bromomethyl)naphthalene/piperidine | 2,3-Bis(piperidinomethyl)naphthalene dihydrochloride, m.p. 253° |
| 11 | 2,3-Bis(bromomethyl)naphthalene/pyrrolidine | 2,3-Bis(pyrrolidin-1-ylmethyl)naphthalene dihydrochloride, m.p. 265° |
| 12 | 2,3-Bis(bromomethyl)naphthalene/hexamethyleneimine | 2,3-Bis(hexamethyleneiminomethyl)naphthalene dihydrochloride m.p. 228° |
| 13 | 2,3-Bis(bromomethyl)naphthalene/1,2,3,6-tetrahydropyridine | 2,3-Bis(1',2',3',6'-tetrahydropyridinomethyl)naphthalene dihydrochloride, m.p. 226° |
| 14 | 2,3-Bis(bromomethyl)naphthalene/2,6-dimethylmorpholine | 2,3-Bis(2',6'-dimethylmorpholinomethyl)naphthalene dihydrochloride, m.p. 240° |
| 15 | 2,3-Bis(bromomethyl)naphthalene/N-methylpiperazine | 2,3-Bis(4-methylpiperazin-1-ylmethyl)naphthalene tetrahydrochloride, m.p. 210° |
| 16 | 2,3-Bis(bromomethyl)naphthalene/N-phenylpiperazine | 2,3-Bis(4-phenylpiperazin-1-ylmethyl)naphthalene dihydrochloride, m.p. 240° |
| 17 | 2,3-Bis(bromomethyl)naphthalene/ethylamine | 2,3-Bis(ethylaminomethyl)naphthalene dihydrochloride, m.p. 304° |
| 18 | 2,3-Bis(bromomethyl)naphthalene/4-methylpiperidine | 2,3-Bis(4'-methylpiperidinomethyl)naphthalene, m.p. 80° |
| 19 | 2,3-Bis(bromomethyl)naphthalene/3-methylpiperidine | 2,3-Bis(3'-methylpiperidinomethyl)naphthalane b.p. 175°/0.2 |
| 20 | 2,3-Bis(bromomethyl)naphthalene/2-methylpiperidine | 2,3-Bis(2'-methylpiperidinomethyl)naphthalene, b.p. 180°/0.2 mm |
| 21 | 1,4-Dichloro-2,3-bis(bromomethyl)-naphthalene*/morpholine | 1,4-Dichloro-2,3-bis(morpholinomethyl)naphthalene dihydrochloride m.p. 230° |
| 22 | 1,4-Dichloro-2,3-bis(bromomethyl)-naphthalene/piperidine | 1,4-Dichloro-2,3-bis(piperidinomethyl)naphthalene m.p. 166° |
| 23 | 1-Chloro-2,3-bis(bromomethyl)naphthalene*/-morpholine | 1-Chloro-2,3-bis(morpholinomethyl)naphthalene dihydrochloride, m.p. 220° |
| 24 | 2,3-Bis(1-phenyl-1-bromomethyl)-naphthalene*/piperidine | 2,3-Bis(1-phenyl-1-piperidinomethyl)naphthalene dihydrochloride, m.p. 184° |
| 25 | 2,3-Bis(1-phenyl-1-bromomethyl)-naphthalene/morpholine | 2,3-Bis(1-phenyl-1-morpholinomethyl)naphthalene dihydrochloride, m.p. 196° |
| 26 | 1,2-Bis(bromomethyl)naphthalene/n-propylamine | 1,2-Bis(n-propylaminomethyl)naphthalene dihydrochloride, m.p. 292° |

*The preparation of these starting materials is described below

As indicated above the compounds according to the invention possess analgesic activity. This analgesic activity has been demonstrated in the acetylcholine-induced writhing test in the mouse using the method generally described by Collier, H. O. J., Denneen, L. C., Johnson, C. A. and Schneider, C. (1968), Br. J. Pharmac., 32, 295–310. A particularly active compound in this test is 2,3-bis-(morpholinomethyl)naphthalene. A preferred pharmaceutically acceptable salt of this compound is the dihydrochloride. This is conveniently isolated as the monohydrate.

The following Examples illustrate the invention:

EXAMPLE 1

2,3-Bis(morpholinomethyl)naphthalene dihydrochloride 2,3-Bis(bromomethyl)naphthalene (8 g) and morpholine (100 ml) were heated under reflux for 6 hours. Excess morpholine was evaporated under reduced pressure and the residue was partitioned between aqueous sodium hydroxide and ether. The ether phase was extracted with 2N-hydrochloric acid, the extract was evaporated to dryness under reduced pressure and the residue was crystallised from aqueous propan-2-ol to give 2,3-bis(morpholinomethyl)naphthalene dihydrochloride, monohydrate, m.p. 244°.

1-Chloro-2,3-bis(bromomethyl)naphthalene

N-Chlorosuccinimide (14 g) in glacial acetic acid (150 ml) was added to 2,3-dimethylnaphthalene (15.6 g) in refluxing glacial acetic acid (150 ml) over 30 min. The solution was evaporated to dryness and the residue was washed with ether (3 × 100 ml) and insoluble material discarded. The ether washings were evaporated and the residue recrystallised from ethanol to give 1-chloro-2,3-dimethylnaphthalene (1) m.p. 55°.

N-Bromosuccinimide (18 g) was added to a solution of the foregoing product (1) (8.0 g) and benzoyl peroxide (0.5 g) in refluxing carbon tetrachloride (120 ml) and the solution was refluxed for 2 hr. The hot solution was filtered and the precipitate discarded; the filtrate was evaporated to dryness and the residue recrystallised from acetone to give 1-chloro-2,3-bis(bromomethyl)naphthalene m.p. 108°.

1,4-Dichloro-2,3-bis(bromomethyl)naphthalene 2,3-Dimethylnaphthalene (15.6 g) and N-chlorosuccinimide (27 g) were refluxed in glacial acetic acid (150 ml) for 1 hr. The precipitate which formed was filtered and recrystallised from ethanol to give 1,4-dichloro-2,3-dimethylnaphthalene (II) m.p. 142°.

N-Bromosuccinimide (21 g) was added to the foregoing product (II) (11 g) and benzoyl peroxide (0.5 g) dissolved in refluxing carbon tetrachloride (200 ml) and the solution was refluxed for 2 hr. The hot solution was filtered and the precipitate discarded; the filtrate was evaporated to dryness and washed with acetone (100 ml), undissolved material was filtered and identified as 1,4-dichloro-2,3-bis(bromomethyl)naphthalene m.p. 150°.

2,3-Bis(1-phenyl-1-bromomethyl)naphthalene 2,3-Naphthalenedicarboxaldehyde (10.0 g) in dry tetrahydrofuran (100ml) was added to phenylmagnesium bromide [derived from bromobenzene (53 g) and magnesium (8 g)] in dry tetrahydrofuran (500 ml) over 1 hr. and the solution was refluxed for a further 3 hr. On cooling, water (500 ml) was added and the ethereal layer was decanted. The aqueous slurry was washed with ether (4 × 500 ml) and the combined ethereal extracts were dried (magnesium sulphate) and evaporated to dryness. The residue was purified by chromatography on silica gel and recrystallised from dichloromethane/petroleum ether (b.p. 40°-60°) to yield two isomers of 2,3-bis(1-phenyl-1-hydroxymethyl)naphthalene (III) (8.0 g. m.p. 145° and 3.0 g, m.p. 164°).

Hydrogen bromide was bubbled through a solution of the foregoing product (III) (3.4 g) in dichloromethane (200 ml) for 30 min. The solvent was evaporated to give 2,3-bis(1-phenyl-1-bromomethyl)naphthalene (4.5 g) as an oil which was used without further purification.

EXAMPLE 27

1,4-Diethoxy-2,3-bis(morpholinomethyl)naphthalene

A mixture of 1,4-diethoxy-2,3-bis(chloromethyl)-naphthalene (VI) (2.5 g) and morpholine (50 ml) was heated under reflux for 4 hours. The precipitated material was filtered off and the filtrate was evaporated. Crystallisation of the residue from light petroleum (b.p. 80°-100°) gave
1,4-diethoxy-2,3-bis(morpholinomethyl)naphthalene, m.p. 136°.

The starting material (VI) was prepared as follows:

a. Diethyl 1,4-diethoxy-2,3-naphthalenedicarboxylate

Iodoethane (70 g) was added to a solution of diethyl 1,4-dihydroxy-2,3-naphthalenedicarboxylate (35 g) in ethanolic sodium ethoxide, prepared from sodium (7.6 g) and ethanol (250 ml), and the mixture was heated under reflux for 3 hours. After keeping overnight at room temperature, the mixture was poured onto ice-hydrochloric acid (500 ml). The oil was separated, washed with aqueous sodium bicarbonate and crystallised from ethanol to give diethyl 1,4-diethoxy-2,3-naphthalenedicarboxylate, (IV) m.p. 68°.

b. 1,4-Diethoxy-2,3-bis(hydroxymethyl)naphthalene

A solution of the foregoing product (IV) (10 g) in anhydrous tetrahydrofuran (100 ml) was added, over ½ hour, to a stirred suspension of lithium aluminium hydride (5 g) in anhydrous tetrahydrofuran (100 ml) and the mixture was heated under reflux for 4 hours. Aqueous sodium hydroxide (100 ml) was added to the cooled mixture, the organic liquids were decanted and the residual slurry was extracted with ether. The extracts were combined, dried over anhydrous magnesium sulphate and evaporated. Crystallisation of the residue from light petroleum (b.p. 80°-100°)/methanol gave 1,4-diethoxy-2,3-bis(hydroxymethyl)naphthalene, (V) m.p. 146°.

c. 1,4-Diethoxy-2,3-bis(chloromethyl)naphthalene

A mixture of the foregoing product (V) (3.75 g) and thionyl chloride (50 ml) was heated under reflux for 3 hrs. Excess thionyl chloride was evaporated and the residue was crystallised from light petroleum (b.p. 40°-60°) to give 1,4-diethoxy-2,3-bis(chloromethyl)-naphthalene, (VI) m.p. 110°.

The following compounds given in a Table a 2 below were prepared in a manner similar to Example 27. The designations (IV), (V) and (VI) are used in a manner similar to that of Example 27.

Table 2

| Example | Intermediates (IV) | (V) | (VI)/Base | Product |
|---|---|---|---|---|
| 28 | Diethyl 1,4-diethoxy-2,3-naphthalenedicarboxylate | 1,4-Diethoxy-2,3-bis-(hydroxymethyl)naphthalene | 1,4-Diethoxy-2,3-bis-(chloromethyl)naphthalene/piperidine | 1,4-Diethoxy-2,3-bis (piperidinomethyl) naphthalene, m.p. 125° |
| 29 | Diethyl 1,4-dimethoxy-2,3-naphthalenedicarboxylate, non-crystalline | 1,4-Dimethoxy-2,3-bis-(hydroxymethyl)naphthalene, m.p. 139° | 1,4-Dimethoxy-2,3-bis-(chloromethyl)naphthalene m.p. 92°/morpholine | 1,4-Dimethoxy-2,3-bis (morpholinomethyl) naphthalene, m.p. 138° |
| 30 | Diethyl 1,4-di-n-butoxy-2,3-naphthalenecarboxylate, non-crystalline | 1,4-Di-n-butoxy-2,3-bis-(hydroxymethyl)naphthalene m.p. 78° | 1,4-Di-n-butoxy-2,3-bis-(chloromethyl)naphthalene non-crystalline/morpholine | 1,4-Di-n-butoxy-2,3-bis-(morpholinomethyl) naphthalene, m.p. 118° |

EXAMPLE 31

1-Phenyl-2,3-bis(morpholinomethyl)naphthalene

1-Phenyl-2,3-bis(chloromethyl)naphthalene (IX) (3.6 g) and morpholine (50 ml) were refluxed for 3 hr. The precipitate was filtered off and the filtrate was evaporated to dryness. The residue was recrystallised from aqueous ethanol to give 1-phenyl-2,3-bis(morpholinomethyl)naphthalene, m.p. 107°, (dihydrochloride m.p. 198°).

The starting material (IX) was prepared as follows:

a. 1-Phenyl-2,3-bis(hydroxymethyl)naphthalene

1-Phenyl-2,3-naphthalenedicarboxylic anhydride (VII) (25 g) was added to lithium aluminium hydride (10.4 g) in refluxing tetrahydrofuran (500 ml) over 30 min. and the reactants were refluxed for a further 1 hr. Water was added and the precipitate formed was filtered off and washed with ether (3 × 500 ml). The filtrate and the combined ether washings were dried (Mg$_2$SO$_4$) and evaporated to dryness. The residue was recrystallised from toluene to give 1-phenyl-2,3-bis(hydroxymethyl)naphthalene (VIII) m.p. 150°.

b. 1-Phenyl-2,3-bis(chloromethyl)naphthalene

1-Phenyl-2,3-bis(hydroxymethyl)naphthalene (7.2 g) (VIII) and thionyl chloride (50 ml) were stirred for 24 hr. Thionyl chloride was evaporated and the residue was recrystallised from light petroleum (b.p. 80° to 100°) to give 1-phenyl-2,3-bis(chloromethyl)naphthalene (IX) m.p. 93°.

The compounds given in Table 3 were prepared in a manner similar to Example 31.

Table 3

| Example | Intermediates (VII) | (VIII) | Product (IX)/Base | |
|---|---|---|---|---|
| 32 | 6-Methyl-2,3-naphthalene-dicarboxylic anhydride | 6-Methyl-2,3-bis-(hydroxymethyl)naphthalene m.p. 156° | 6-Methyl-2,3-bis-(chloromethyl)naphthalene m.p. 84°/morpholine | 6-Methyl-2,3-bis-(morpholinomethyl) naphthalene dihydrochloride m.p. 254° |
| 33 | 6-Chloro-2,3-naphthalene-dicarboxylic anhydride,* m.p. 220° | 6-Chloro-2,3-bis-(hydroxymethyl)naphthalene m.p. 125° | 6-Chloro-2,3-bis-(chloromethyl)naphthalene m.p. 70°/morpholine | 6-Chloro-2,3-bis-(morpholinomethyl) naphthalene dihydrochloride, m.p. 250° |
| 34 | " | " | 6-Chloro-2,3-bis-(chloromethyl)naphthalene m.p. 70°/piperidine | 6-Chloro-2,3-bis-(piperidinomethyl) naphthalene, m.p. 102° |
| 35 | 5-Chloro-2,3-naphthalene dicarboxylic anhydride,* m.p. 234° | 5-Chloro-2,3-bis-(hydroxymethyl)naphthalene m.p. 104° | 5-Chloro-2,3-bis(chloromethyl)naphthalene, m.p. 90°/morpholine | 5-Chloro-2,3-bis-(morpholinomethyl) naphthalene dihydrochloride, m.p. 245° |
| 36 | 6-Fluoro-2,3-naphthalene dicarboxylic anhydride,* m.p. 204° | 6-Fluoro-2,3-bis-(hydroxymethyl) naphthalene, m.p. 132° | 6-Fluoro-2,3-bis(chloromethyl)naphthalene/morpholine | 6-Fluoro-2,3-bis-(morpholinomethyl) naphthalene dihydrochloride, m.p. 242° |

*The production of these compounds is described later

EXAMPLE 37

5-Chloro-6-methoxy-2,3-bis(morpholinomethyl)-naphthalene dihydrochloride

6-Methoxy-2,3-bis(hydroxymethyl)naphthalene (0.2 g m.p. 142°) [prepared by reduction of 6-methoxy-2,3-naphthalene dicarboxylic anhydride, the preparation of which is described after Examples 38 and 39 with lithium aluminium hydride] was added to a solution of phosphorus pentachloride (0.8 g) in phosphoryl chloride (10 ml) and stirred at room temperature for 3 hours. The solution was evaporated to dryness and the residue was extracted with hot petroleum ether (b.p. 80°-100°); the washings were concentrated and the precipitate which formed, was filtered to give 5-chloro-6-methoxy-2,3-bis(chloromethyl)naphthalene (X) m.p. 103°.

Compound (X) was also formed when 6-methoxy-2,3-bis(hydroxymethyl)naphthalene was treated with thionyl chloride in a manner analogous to that described in Example 31.

(X) (0.2 g) and morpholine (50 ml) were refluxed for 3 hours. The precipitate which formed was filtered and the filtrate was evaporated to dryness. The residue was partitioned between aqueous sodium hydroxide and ether. The ether phase was extracted with 2N-hydrochloric acid and the aqueous extract was evaporated to dryness to leave a residue which was recrystallised from methanol/carbon tetrachloride to give 5-chloro-6-methoxy-2,3-bis(morpholinomethyl)naphthalene dihydrochloride, m.p. 268°.

EXAMPLES 38 and 39

5-Bromo-6-methoxy- and 6-methoxy-2,3-bis(morpholinomethyl) naphthalenes.

Bromine (3.2 g) was added to triphenylphosphine (6.0 g) and 6-methoxy-2,3-bis(hydroxymethyl)naphthalene (2.2 g) in dimethylformamide (50 ml) kept at 0°. The solution was stirred for 30 min. and volatile material was then evaporated at reduced pressure. The residue was partitioned between ether and water, the ether layer was dried (magnesium sulphate) and evaporated to dryness to leave an oil (XI) which was used without further purification.

The foregoing oil (XI) and morpholine (100 ml) were refluxed for 3 hours. The precipitate which formed on cooling, was filtered and the filtrate was evaporated to dryness; the residue was partitioned between aqueous sodium hydroxide and ether. The ethereal layer was evaporated to dryness and the residue was purified by column chromatography (eluent, diethylamine:cyclohexane = 1:5 silica) to give two products, both of which were recrystallised from light petroleum (b.p. 60°-80°), which were identified as 6-methoxy-2,3-bis(morpholinomethyl)naphthalene m.p. 82° (dihydrochloride, m.p. 266°) and 5-bromo-6-methoxy-2,3-bis(morpholinomethyl)naphthalene, m.p. 142°.

The novel starting materials mentioned in Table 3 and in Example 37 were prepared as follows:

6-Chloro-2,3-naphthalene dicarboxylic anhydride p-Chlorophenylpropiolic acid (3.3 g) and propiolic acid (7.6 g) in acetic anhydride (80 ml) were refluxed for 12 hr. The solution was concentrated (to 40 ml) and the precipitate which formed on cooling was recrystallised from acetone to give 6-chloro-2,3-naphthalenedicarboxylic anhydride (2.3 g) m.p. 220°.

Similarly prepared from p-methoxyphenylpropiolic acid and propiolic acid was 6-methoxy-2,3-naphthalenedicarboxylic anhydride (m.p. 244°); from p-fluorophenylpropiolic acid and propiolic acid was prepared 6-fluoro-2,3-naphthalenedicarboxylic anhydride (m.p. 204°) and from o-chlorophenylpropiolic acid and propiolic acid was prepared 5-chloro-2,3-naphthalenedicarboxylic anhydride (crude sample m.p. 234°).

EXAMPLE 40

2,3-Bis(piperidinomethyl)naphthalene dihydrochloride

To a stirred solution of 2-piperidinomethylnaphthalene (5.6 g) in dry ether (200 ml) was added, under nitrogen, a 1.5M ethereal solution of butyl lithium (18.3 ml) and the mixture was kept at room temperature for 24 hours. N-(Chloromethyl)piperidine (7.34 g) was added, the mixture was heated under reflux for 1 hour, and poured into water (1 l). The precipitated material was extracted into ether, the extract was washed with water, dried over anhydrous magnesium sulphate and evaporated to dryness. The residue was purified by chromatography on silica and an ethereal solution of the product was treated with ethereal hydrogen chloride. 1,2-Bis(piperidinomethyl)naphthalene dihydrochloride crystallised from propan-2-ol as prisms, m.p. 240°.

EXAMPLE 41

1-Morpholinomethyl-2-piperidinomethylnaphthalene dihydrochloride, m.p. 243°-244° was prepared in a manner similar to Example 40 from 2-piperidinomethylnaphthalene and chloromethylmorpholine.

EXAMPLE 42

Preparation of a quaternary ammonium salt 2,3-Bis(morpholinomethyl)naphthalene dimethiodide 2,3-Bis(morpholinomethyl)naphthalene dihydrochloride (Example 1) (10 g) was partitioned between aqueous sodium hydroxide and ether. The ethereal layer was evaporated to dryness and the residue was heated under reflux with acetone (100 ml) and iodomethane (30 ml) for 24 hours. The precipitated material was collected and crystallised from isopropanol-water to give 2,3-bis(morpholinomethyl)naphthalene dimethiodide, m.p. 212°.

EXAMPLE 43

2-Diethylaminomethyl-3-morpholinomethylnaphthalene a. 2,2-Diethylbenz[f]isoindolinium bromide An ethanolic diethylamine solution (100 ml) was added dropwise to 2,3-bis(bromomethyl)naphthalene (20 g) in ethanol (10 ml) kept at 0°. The precipitate which formed was filtered and recrystallised from propan-2-ol/water to give 2,2-diethylbenz[f]isoindolinium bromide m.p. 228°.

Similarly prepared from 2,3-bis(bromomethyl)naphthalene and ethylmethylamine was 2-ethyl-2-methylbenz[f]isoindolinium bromide m.p. 208°, and from 2,3-bis(bromomethyl)naphthalene and di-n-butylamine was 2,2-di-n-butylbenz[f]isoindolinium bromide.

b. 2-Diethylaminomethyl-3-morpholinomethylnaphthalene 2,2-Diethylbenz[f]isoindolinium bromide (13 g) was refluxed with morpholine (150 ml) for 30 hr. Morpholine was evaporated and the residue was partitioned between sodium hydroxide solution and ether; the ether layer was evaporated to dryness and the residue purified by chromatography [eluent, diethylamine:cyclohexane = 1:4, silica (250 g)] and distillation to give 2-diethylaminomethyl-3-morpholinomethylnaphthalene, b.p. 160°/0.015 mm.

The following compounds were prepared similarly.

| Ex. | |
|---|---|
| 44 | 2-Dimethylaminomethyl-3-morpholinomethylnaphthalene dihydrochloride, m.p. 234° from 2,2-dimethylbenz[f]isoindolinium bromide and morpholine. |
| 45 | 2-Dimethylaminomethyl-3-piperidinomethylnaphthalene, b.p. 140°/0.04 mm from 2,3-dimethylbenz[f]isoindolinium bromide and piperidine in n-hexanol. |
| 46 | 2-Morpholinomethyl-3-piperidinomethylnaphthalene, dihydrochloride, m.p. 226° from 2,2-pentamethylenebenz[f]isoindolinium bromide and morpholine. |
| 47 | 2-Diethylamino-3-piperidinomethylnaphthalene, b.p. 145°/0.04 mm from 2,2-diethylbenz[f]isoindolinium bromide and piperidine in n-hexanol. |
| 48 | 2-(N-Methyl-N-ethylaminomethyl)-3-piperidinomethyl naphthalene from 2-methyl-2-ethylbenz[f]isoindolinium bromide and piperidine in n-hexanol. |
| 49 | 2-Piperidinomethyl-3-[pyrrolidin-1-yl-methyl]naphthalene, b.p. 150°/0.04 mm, m.p. 73° from 2,2-pentamethylenebenz[f]isoindolinium bromide and pyrrolidine in n-hexanol. |
| 50 | 2-n-Butylaminomethyl-3-diethylaminomethylnaphthalene, b.p. 160°/0.04 mm from 2,2-diethylbenz[f]isoindolinium bromide and n-butylamine in n-hexanol. |
| 51 | 2-Di-n-butylaminomethyl-3-piperidinomethylnaphthalene, b.p. 200°/0.08 mm from 2,2-di-n-butyl-benz[f]isoindolinium bromide and piperidine in n-hexanol. |

EXAMPLE 52

2,3-Bis(morpholinomethyl)naphthalene dihydrochloride

Dimethyl 2,3-naphthalenedicarboxylate (2 g) and morpholine (100 ml) were kept at 100° for 6 days. Morpholine was evaporated and the residual oil (3.2 g) was dissolved in dry tetrahydrofuran (25 ml) and added dropwise to lithium aluminium hydride (1.5 g) in tetrahydrofuran (100 ml) over 30 minutes. After refluxing for 2 hours, the solution was cooled and water was added. The ethereal layer was decanted and the residual slurry was washed with ether (3 × 100 ml). The combined ethereal extracts were dried, (magnesium sulphate) and extracted with aqueous hydrochloric acid. The aqueous layer was evaporated to dryness and the residue was recrystallised (charcoal) from propan-2-ol to give 2,3-bis(morpholinomethyl)naphthalene dihydrochloride, m.p. 244°.

EXAMPLE 53

Pharmaceutical Compositions (In this Example the compound of Example 1 is used as the active compound in the form of the monohydrate, that is 2,3-bis(morpholinomethyl)naphthalene dihydrochloride monohydrate. This is referred in the Example as the active compound)

| Tablet formula (per tablet) | |
|---|---|
| (1) Filmcoated tablet | |
| Active compound | 65.0 mg |
| Sucrose | 129.0 mg |
| Polyvinylpyrrolidone | 4.0 mg |
| Magnesium stearate | 2.0 mg |
| Tablet weight | 200.0 mg |

Method

Blend the active compound with sucrose by gradual dilution and granulate the powders with an alcoholic solution of polyvinylpyrrolidone. Pass the granulate through a No. 12 mesh screen or mechanical granulator. Dry the granules in a hot air oven at 40° C and screen through No. 20 mesh. Blend the magnesium stearate with the granules and compress on a tablet machine fitted with 8 mm. punches.

The tablets may be filmcoated by intermittent or continuous spray methods using acceptable film forming materials and colouring matter.

| (2) Press-coated tablet | |
|---|---|
| Tablet Core | |
| Active compound | 65.0 mg |
| Lactose | 51.4 mg |
| Polyvinylpyrrolidone | 2.4 mg |
| Magnesium stearate | 1.2 mg |
| Core weight | 120.0 mg |
| Tablet Coating | |
| Lactose | 214.2 mg |
| Maize starch | 61.6 mg |
| Lake colouring matter | 1.4 mg |
| Magnesium stearate | 2.8 mg |

-continued

| | |
|---|---|
| Coating weight | 280.0 mg |
| Total tablet weight | 400.0 mg |

Method

1. Prepare the granules for the tablet core by granulating a blend of the active compound and lactose with an alcoholic solution of polyvinylpyrrolidone. Pass the granulate through a No. 16 mesh screen or mechanical granulator. Dry the granules in a hot air oven at 40° C and screen through No. 20 mesh screen. Blend the magnesium stearate with the granules.

2. Prepare the granules for the coating by granulating a blend of lactose, starch, and colour with 10% starch paste. Pass the granulate through a No. 12 mesh screen or mechanical granulator. Dry the granules in a hot air oven at 40° C and screen through No. 20 mesh screen. Blend the magnesium stearate with the granules.

Tablets are compressed on a Manesty Dry-Cota machine, compressing the core on the lefthand section and the coating on the righthand section.

Other active ingredients e.g. caffein may be included in the coating by substituting a proportion of the lactose content. The lactose may be replaced by either a third active ingredient or alternative inert excipient. An alternative binding agent could also replace the starch paste.

We claim:

1. A compound of the formula $$\text{(I)}$$

with substituents $CHR^1NR^2R^3$ and $CHR^4NR^5R^6$ on a naphthalene ring wherein $R^1$ and $R^4$ are hydrogen or phenyl; the group $CHR^4NR^5R^6$ is in the 1 or 3 position; $R^2$ and $R^3$ are $C_{1-6}$ alkyl or monohydroxy $C_{1-6}$ alkyl; $R^5$ and $R^6$ are hydrogen or $C_{1-6}$ alkyl; $R^2$ and $R^3$ or $R^5$ and $R^6$ form together with the nitrogen atom piperidino, mono methyl piperidino, morpholino, 2,6-dimethyl morpholino, pyrrolidino, piperazino, N-methyl-or phenyl-piperazino, tetrahydro pyridino or hexamethylene-imino, at least one of $R^2$ and $R^3$ or $R^5$ and $R^6$ being morpholino or 2,6-dimethyl morpholino; the naphthalene nucleus being unsubstituted or mono substituted by $C_{1-6}$ alkyl, $C_{1-6}$ alkoxy, a halogen atom or phenyl, or disubstituted at the 1 and 4 positions by halogen, at the 1 and 4 positions by $C_{1-6}$ alkoxy or at the 5-position by a halogen atom and the 6-position by $C_{1-6}$ alkoxy; or a pharmaceutically acceptable acid addition, or a methiodide quaternary salt, or a hydrate thereof.

2. The compound of claim 1 which is 2,3-bis(morpholinomethyl) naphthalene or a pharmaceutically acceptable acid addition or methiodide quaternary salt thereof.

3. The compound of claim 2 which is 2,3-bis(morpholinomethyl)naphthalene dihydrochloride.

4. The compound of claim 1 which is 2,3-bis-(morpholinomethyl)naphthalene, dihydrochloride, monohydrate.

5. An analgesic composition consisting essentially of a compound as defined in claim 1 together with a pharmaceutical non-toxic carrier or diluent.

6. A composition as claimed in claim 5 in a form suitable for oral administration.

7. A composition as claimed in claim 6 in dosage unit form as a tablet or capsule each dosage unit containing an amount of active ingredient within the range of 5–100 mg per dosage unit.

8. A method of relieving pain in a patient comprising administering to said patient an effective amount of a compound as claimed in claim 1.

9. The compound of claim 1, which is 1,2-bis(morpholinomethyl)naphthalene or a pharmaceutically acceptable acid addition or methiodide quaternary salt thereof.

10. The compound of claim 1 which is 2,3-bis(2',6'-dimethylmorpholinomethyl)naphthalene or a pharmaceutically acceptable acid addition or methiodide quaternary salt thereof.

11. The compound of claim 1 which is 1,4-dichloro-2,3-bis(morpholinomethyl)naphthalene or a pharmaceutically acceptable acid addition or methiodide quaternary salt thereof.

12. The compound of claim 1 which is 1-chloro-2,3-bis(morpholinomethyl)naphthalene or a pharmaceutically acceptable acid addition or methiodide quaternary salt thereof.

13. The compound of claim 1 which is 2,3-bis(1-phenyl-1-morpholinomethyl)naphthalene or a pharmaceutically acceptable acid addition or methiodide quaternary salt thereof.

14. The compound of claim 1 which is 1,4-diethoxy-2,3-bis(morpholinomethyl)naphthalene or a pharmaceutically acceptable acid addition or methiodide quaternary salt thereof.

15. The compound of claim 1 which is 1,4-dimethoxy-2,3-bis(morpholinomethyl)naphthalene or a pharmaceutically acceptable acid addition or methiodide quaternary salt thereof.

16. The compound of claim 1 which is 1,4-di-n-butoxy-2,3-bis(morpholinomethyl)naphthalene or a pharmaceutically acceptable acid addition or methiodide quaternary salt thereof.

17. The compound of claim 1 which is 1-phenyl-2,3-bis(morpholinomethyl)naphthalene or a pharmaceutically acceptable acid addition or methiodide quaternary salt thereof.

18. The compound of claim 1 which is 6-methyl-2,3-bis(morpholinomethyl)naphthalene or a pharmaceutically acceptable acid addition or methiodide quaternary salt thereof.

19. The compound of claim 1 which is 6-chloro-2,3bis(morpholinomethyl)naphthalene or a pharmaceutically acceptable acid addition or methiodide quaternary salt thereof.

20. The compound of claim 1 which is 5-chloro-2,3bis(morpholinomethyl)naphthalene or a pharmaceutically acceptable acid addition or methiodide quaternary salt thereof.

21. The compound of claim 1 which is 6-fluoro-2,3bis(morpholinomethyl)naphthalene or a pharmaceutically acceptable acid addition or methiodide quaternary salt thereof.

22. The compound of claim 1 which is 5-chloro-6-methoxy-2,3-bis(morpholinomethyl)naphthalene or a pharmaceutically acceptable acid addition or methiodide quaternary salt thereof.

23. The compound of claim 1 which is 5-bromo-6-methoxy-2,3-bis(morpholinomethyl)naphthalene or a pharmaceutically acceptable acid addition or methiodide quaternary salt thereof.

24. The compound of claim 1 which is 6-methoxy-2,3bis(morpholinomethyl)naphthalene or a pharmaceutically acceptable acid addition or methiodide quaternary salt thereof.

25. The compound of claim 1 which is 1-morpholinomethyl-2-piperidinomethylnaphthalene or a pharmaceutically acceptable acid addition or methiodide quaternary salt thereof.

26. The compound of claim 1 which is 2,3-bis(morpholinomethyl)naphthalene dimethiodide.

27. The compound of claim 1 which is 2-diethylaminomethyl-3-morpholinomethylnaphthalene or a pharmaceutically acceptable acid addition or methiodide quaternary salt thereof.

28. The compound of claim 1 which is 2-dimethylaminomethyl-3-morpholinomethylnaphthalene or a pharmaceutically acceptable acid addition or methiodide quaternary salt thereof.

29. The compound of claim 1 which is 2-morpholinomethyl-3-piperidinomethylnaphthalene or a pharmaceutically acceptable acid addition or methiodide quaternary salt thereof.

* * * * *